(12) United States Patent
Ujihara

(10) Patent No.: US 6,420,569 B1
(45) Date of Patent: Jul. 16, 2002

(54) PROCESS FOR PRODUCING PYRONE COMPOUNDS

(75) Inventor: Kazuya Ujihara, Minoo (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/940,470

(22) Filed: Aug. 29, 2001

(30) Foreign Application Priority Data

Sep. 29, 2000 (JP) ........................................ 2000-299319

(51) Int. Cl.7 ............................................. C07D 309/30
(52) U.S. Cl. ........................................ 549/211
(58) Field of Search ........................................ 549/292

(56) References Cited

FOREIGN PATENT DOCUMENTS

JP           41-20720        12/1966

OTHER PUBLICATIONS

J. L. Douglas et al., "Pyrone studies. Linear α–pyrone route to protected β–polyketones", *Canadian Journal of Chemistry*, vol. 46, 1968, pp. 695–700.

H. Reimlinger, "Transformation of aromatic ketones into ethynyl–derivatives", *Chemistry and Industry*, 1969, pp. 1306–1307.

Luisa Cook et al., "Inhibition of Human Sputum Elastase by Substituted 2–Pyrones", *J. Med. Chem.*, vol. 30, 1987, pp. 1017–1023.

I. F. Kogl et al., "Derivatives of 2,3–dihydropyran–2,4–dione", *Rec. trav. chim.*, vol. 71, 1952, pp. 779–797.

Chemical Abstracts, vol. 64, No. 9, 1966, Abstract No. 12647ef, XP–002185772.

*Primary Examiner*—Amelia Owens
(74) *Attorney, Agent, or Firm*—Sughrue Mion, PLLC

(57) ABSTRACT

4-Hydroxy-6-methyl-3-(4-methyl-2-pentenoyl)-2-pyrone isobtained by allowing 2,3-dihydro-7-methyl-2-(1-methylethyl)-4H,5H-pyrano[4,3-b]pyran-4,5-dione to react with at least one inorganic compound selected from alkali hydroxides, alkaline earth hydroxides, alkali carbonates, alkaline earth carbonates and alkali fluorides in an alcohol, water or a mixture thereof.

14 Claims, No Drawings

PROCESS FOR PRODUCING PYRONE COMPOUNDS

FIELD OF THE INVENTION

The present invention relates to a process for producing 4-hydroxy-6-methyl-3-(4-methyl-2-pentenoyl)-2-pyrone. In more details, it relates to a process for producing 4-hydroxy-6-methyl-3-(4-methyl-2-pentenoyl)-2-pyrone from 2,3-dihydro-7-methyl-2-(1-methylethyl)-4H,5H-pyrano[4,3-b]pyran-4,5-dione.

BACKGROUND ARTS

4-Hydroxy-6-methyl-3-(4-methylpentanoyl)-2-pyrone of formula (1):

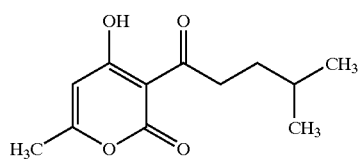

(1)

is a compound which can be utilized as an active ingredient of insecticides, and it can be obtained by a catalytic reduction of 4-hydroxy-6-methyl-3-(4-methyl-2-pentenoyl).-2-pyrone of formula (2):

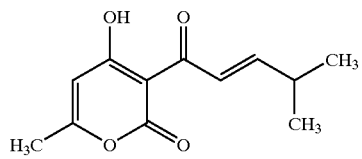

(2)

Therefore, it is useful to afford a process for producing the compound of formula (2).

The present invention has a subject to provide a process for producing 4-hydroxy-6-methyl-3-(4-methyl-2-pentenoyl)-2-pyrone that is an intermediate compound for man manufacturing 4-hydroxy-6-methyl-3-(4-methylpentanoyl)-2-pyrone.

SUMMARY OF THE INVENTION

The present invention provides a process for producing 4-hydroxy-6-methyl-3-(4-methyl-2-pentenoyl)-2-pyrone of formula (2) from 2,3-dihydro-7-methyl-2-(1-methylethyl)-4H,5H-pyrano [4,3-b]pyran-4,5-dione of formula (3):

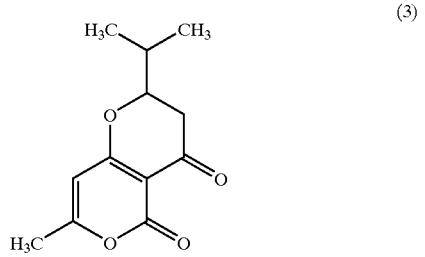

(3)

under a specific condition. 4-Hydroxy-6-methyl-3-(4-methyl-2-pentenoyl)-2-pyrone of formula(2)can be derived to an insecticidal active ingredient, 4-hydroxy-6-methyl-3-(4-methylpentanoyl)-2-pyrone, by a catalytic reduction procedure.

Namely, the present invention provides a process for producing 4-hydroxy-6-methyl-3-(4-methyl-2-pentenoyl)-2-pyrone which comprises allowing 2,3-dihydro-7-methyl-2-(1-methylethyl)-4H, 5H-pyrano[4,3-b]pyran-4,5-dione to react with at least one inorganic compound selected from alkali hydroxides, alkaline earth hydroxides, alkali carbonates, alkaline earth carbonates and alkali fluorides in an alcohol, water or a mixture thereof.

DETAILED DESCRIPTION OF THE INVENTION

The process of the present invention is carried out in an alcohol, water or a mixture thereof.

Examples of the alcohol used for the reaction include lower alcohols, for example, C1–C5 alcohols. Typical examples are methanol, ethanol, 2-propanol and 2-methyl-2-propanol. A mixture of the lower alcohol with water can be utilized as well as a mixture of two or more of the lower alcohols.

In the present invention, the other solvent that is inert to the reaction of the present invention can be used together.

Therefore, the phrase "in an alcohol, water or a mixture thereof" means "in the presence of at least one solvent selected from alcohols and water, and the amount of the solvent is enough for dissolving the inorganic compound selected from alkali hydroxides, alkaline earth hydroxides, alkali carbonates, alkaline earth carbonates and alkali fluorides." The amount of the solvent selected from alcohols and water is usually 1 ml to 1000 ml based on 1 g of 2,3-dihydro-7-methyl-2-(1-methylethyl)-4H,5H-pyrano[4,3-b]pyran-4,5-dione.

Examples of the inert solvent include aliphatic hydrocarbons (e.g. hexane), aromatic hydrocarbons (e.g. toluene), ketones (e.g. methylisobutylketone), esters (e.g. ethyl acetate), ethers (e.g. tetrahydrofuran, diethyl ether), amides (e.g. N,N-dimethylformamide), halogenated hydrocarbons (e.g. chloroform), dimethyl sulfoxide, aliphatic nitriles (e.g. acetonitrile), tertiary amines (e.g. triethylamine) and nitrogen-containing aromatic heterocycles (e.g. pyridine).

Examples of the alkali hydroxide include lithium hydroxide, sodium hydroxide and potassium hydroxide, and examples of the alkaline earth hydroxide include magnesium hydroxide, calcium hydroxide and barium hydroxide. In the present invention, alkali carbonate means normal salt of alkali metal carbonate. Therefore, examples of the alkali carbonate include lithium carbonate, sodium carbonate and potassium carbonate. Examples of the alkaline earth carbonate include magnesium carbonate, calcium carbonate and barium carbonate. Examples of the alkali fluoride include cesium fluoride.

An amount of the alkali hydroxides, alkaline earth hydroxides, alkali carbonates alkaline earth carbonates or alkali metal fluorides used for the reaction is usually 1 to 10 moles, preferable 1 to 5 moles against 1 mole of a starting material, 2,3-dihydro-7-methyl-2-(1-methylethyl)-4H,5H-pyrano[4,3-b]pyran-4,5-dione.

The reaction temperature for the process of the invention is usually -20 to 100° C., provided that it is usually under a boiling point of a solvent when the boiling point of the solvent used for the reaction is below 100° C. The reaction period varies depending on the other reaction conditions and it is usually momentary to 24 hours.

The starting material for the process of the invention, 2,3-dihydro-7-methyl-2-(1-methylethyl)-4H,5H-pyrano[4,3-b]pyran-4,5-dione, can be prepared by a condensation reaction of dehydroacetic acid with isobutyraldehyde in the presence of piperidine in chloroform according to the description of Chemistry and Industry pp. 1306–1307 (1969).

Further, 4-hydroxy-6-methyl-3-(4-methyl-2-pentenoyl)-2-pyrone obtained by the process of the invention can be subjected to a reduction, such as hydrogenation in the presence of a transition metal catalyst, to give 4-hydroxy-6-methyl-3-(4-methylpentanoyl)-2-pyrone that is useful as an active ingredient of insecticides.

EXAMPLES

Hereinafter, the present invention is further illustrated by production examples and so on in detail, although the present invention is not limited in any sense to these examples.

Production Example 1

In 10 ml of methanol, 222 mg of 2, 3-dihydro-7-methyl-2-(1-methylethyl)-4H, 5H-pyrano[4,3-b]pyran-4,5-dione were dissolved, and 200 mg of potassium hydroxide were added thereto and stirred at room temperature for 1 hour. After that, methyl t-butyl ether and 3% hydrochloric acid were added to the reaction mixture. The separated organic layer was washed with saturated brine once, dried over anhydrous magnesium sulfate and concentrated under reduced pressure to give 130 mg of 4-hydroxy-6-methyl-3-(4-methyl-2-pentenoyl)-2-pyrone. $^1$H-NMR (CDCl$_3$, TMS) δ (ppm): 1.13 (6H, d), 2.27 (3H, s), 2.60 (1 H, m), 5.93 (1H, s), 7.23 (1H, dd), 7.58 (1H, d).

Production Example 2

To a mixture of 450 mg of 2, 3-dihydro-7-methyl-2-(1-methylethyl)-4H,5H-pyrano[4,3-b]pyran-4,5-dione and 40 ml of 2-propanol, 400 mg of potassium carbonate were added and stirred at room temperature for 12 hours. The reaction mixture was then concentrated, and methyl t-butyl ether and 3% hydrochloric acid were added thereto. The separated organic layer was washed with saturated brine once, dried over anhydrous magnesium sulfate and concentrated under reduced pressure to give 340 mg of 4-hydroxy-6-methyl- 3-(4-methyl-2-pentenoyl)-2-pyrone.

Production Example 3

To a mixture of 200 mg of 2, 3-dihydro-7-methyl-2-(1-methylethyl)-4H,5H-pyrano[4,3-b]pyran-4,5-dione and 10 ml of water, 200 mg of lithium hydroxide monohydrate were added and stirred at room temperature for 1 hour. After that, methylt-butyl ether and 3% hydrochloric acid were added to the reaction mixture. The separated organic layer was washed with saturated brine once, dried over anhydrous magnesium sulfate and concentrated under reduced pressure to give 178 mg of 4-hydroxy-6-methyl-3-(4-methyl-2-pentenoyl)-2-pyrone.

Production Example 4

A mixture of 108 mg of 2,3-dihydro-7-methyl-2-(1-methylethyl)-4H, 5H-pyrano[4,3-b]pyran-4,5-dione, 200 mg of cesium fluoride and 5ml of 2-methyl-2-propanol was stirred for 2 hours under reflux-heating. After that, methyl t-butyl ether and 3% hydrochloric acid were added to the reaction mixture. The separated organic layer was washed with saturated brine once, dried over anhydrous magnesium sulfate and concentrated under reduced pressure to give 86 mg of 4-hydroxy-6-methyl-3-(4-methyl-2-pentenoyl)-2-pyrone.

Production Example 5

To a mixture of 189 mg of 2,3-dihydro-7-methyl-2-(1-methylethyl)- 4H, 5H-pyrano[4,3-b]pyran-4,5-dione, 4mlof-toluene and 4 ml of water, 0.20 g of sodium hydroxide was added and stirred. After 4 hours, methyl t-butyl ether and 3% hydrochloric acid were added to the reaction mixture. The separated organic layer was washed with saturated brine once, dried over anhydrous magnesium sulfate and concentrated under reduced pressure to give 82 mg of 4-hydroxy-6-methyl-3-(4-methyl-2-pentenoyl)-2-pyrone.

Next, a process for producing 4-hydroxy-6-methyl-3-(4-methylpentanoyl)-2-pyrone by reducing 4-hydroxy-6-methyl-3-(4-methyl-2-pentenoyl)-2-pyrone is illustrated as reference production example.

Reference Production Example

Undernitrogen, 2.8 g of 4-hydroxy-6-methyl-3-(4-methyl-2-pentenoyl)-2-pyrone was dissolved in ethyl acetate and 0.14 g of 5% palladium/carbon was added thereto. The nitrogen in the reaction vessel was substituted by hydrogen and the reaction mixture was stirred at room temperature for 5 hours. After that, the reaction mixture was filtered through a Celite pad and the Celite pad was washed with 50 ml of ethyl acetate. The solution combined the filtrate with the washing solution was washed with 0.1% hydrochloric acid once, water twice and saturated brine once, subsequently. The organic layer was dried over anhydrous magnesium sulfate and concentrated under reduced pressure to give a residue, which was subjected to silica gel column chromatography (eluent: hexane/ethyl acetate =6/1) to give 2.68 g of 4-hydroxy-6-methyl-3-(4-methylpentanoyl)-2-pyrone.

$^1$H-NMR (CDCl$_3$, TMS) δ (ppm): 0.94 (6H, d), 1.54 (2H, q), 1.63 (1H, m), 2.27 (3H, s), 3.08 (2H, t), 5.93 (1H, s), 17.88 (1H, s).

Furthermore, it is shown by reference example that 4-hydroxy-6-methyl-3-(4-methylpentanoyl)-2-pyrone obtained above is useful as an active ingredient of insecticides.

REFERENCE EXAMPLE (Knock-down Test Against Housefly)

A half part of 4-hydroxy-6-methyl-3-(4-methylpentanoyl)-2-pyrone was dissolved in 10 parts of dichloromethane and mixed with 89.5 parts of Isopar M (isoparaffin produced by Exxon Chemical) for preparing 0.5% oil solution. Part(s) means part(s) by weight.

Ten adult houseflies (*Musca domestica*) including 5 males and 5 females were released in a 70 cm-cubic glass chamber (volume: 0.34 cm$^3$). By a spray-gun, 0.7 ml of the above oil solution was applied at a pressure of 0.9 kg/cm$^2$ from a small window on the wall of the chamber. After 15 minutes from application, knocked-down houseflies were observed. As a result of two repetitions, the knocked-down ratio was 95%.

What is claimed is:

1. A process for producing 4-hydroxy-6-methyl-3-(4-methyl-2-pentenoyl)-2-pyrone which comprises allowing 2,3-dihydro-7-methyl-2-(1-methylethyl)-4H,5H-pyrano[4,3-b]pyran-4,5-dione to react with at least one inorganic compound selected from alkali hydroxides, alkaline earth hydroxides, alkali carbonates, alkaline earth carbonates and alkali fluorides in an alcohol, water or a mixture thereof.

2. A process for producing 4-hydroxy-6-methyl-3-(4-methyl-2-pentenoyl)-2-pyrone which comprises allowing 2,3-dihydro-7-methyl-2-(1-methylethyl)-4H,5H-pyrano[4,3-b]pyran-4,5-dione to react with at least one inorganic compound selected from alkali hydroxides, alkaline earth hydroxides, alkali carbonates, alkaline earth carbonates and alkali fluorides in an alcohol.

3. A process for producing 4-hydroxy-6-methyl-3-(4-methyl-2-pentenoyl)-2-pyrone which comprises allowing 2,3-dihydro-7-methyl-2-(1-methylethyl)-4H,5H-pyrano[4,3-b]pyran-4,5-dione to react with at least one inorganic compound selected from alkali hydroxides, alkaline earth hydroxides, alkali carbonates, alkaline earth carbonates and alkali fluorides in water.

4. A process according to claim 1, wherein the inorganic compound is an alkali hydroxide.

5. A process according to claim 4, wherein the alkali hydroxide is lithium hydroxide, sodium hydroxide or potassium hydroxide.

6. A process according to claim 1, wherein the inorganic compound is an alkaline earth hydroxide.

7. A process according to claim 6, wherein the alkaline earth hydroxide is magnesium hydroxide, calcium hydroxide or barium hydroxide.

8. A process according to claim 1, wherein the inorganic compound is an alkali carbonate.

9. A process according to claim 8, wherein the alkali carbonate is lithium carbonate, sodium carbonate or potassium carbonate.

10. A process according to claim 1, wherein the inorganic compound is an alkaline earth carbonate.

11. A process according to claim 10, wherein the alkaline earth carbonate is magnesium carbonate, calcium carbonate or barium carbonate.

12. A process according to claim 1, wherein the inorganic compound is an alkali fluoride.

13. A process according to claim 12, wherein the alkali fluoride is cesium fluoride.

14. A process according to claim 1, wherein the reaction temperature is $-20$ to $100°$ C.

* * * * *